(12) United States Patent
Dronov et al.

(10) Patent No.: US 8,666,504 B2
(45) Date of Patent: Mar. 4, 2014

(54) COMMUNICATION AND CHARGING CIRCUITRY FOR A SINGLE-COIL IMPLANTABLE MEDICAL DEVICE

(75) Inventors: Vasily Dronov, San Jose, CA (US); Jordi Parramon, Valencia, CA (US); Robert Ozawa, Woodland Hills, CA (US); Md. Mizanur Rahman, Stevenson Ranch, CA (US); Emanuel Feldman, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/608,490

(22) Filed: Sep. 10, 2012

(65) Prior Publication Data
US 2013/0103115 A1     Apr. 25, 2013

Related U.S. Application Data

(60) Provisional application No. 61/550,588, filed on Oct. 24, 2011.

(51) Int. Cl.
*A61N 1/05* (2006.01)

(52) U.S. Cl.
USPC .......................................................... 607/60

(58) Field of Classification Search
USPC .......................................................... 607/60
See application file for complete search history.

(56) References Cited

U.S. PATENT DOCUMENTS

| | | | |
|---|---|---|---|
| 5,733,313 A * | 3/1998 | Barreras et al. | 607/33 |
| 7,444,181 B2 | 10/2008 | Shi et al. | |
| 8,081,925 B2 | 12/2011 | Parramon et al. | |
| 8,155,752 B2 | 4/2012 | Aghassian et al. | |
| 2001/0002441 A1 | 5/2001 | Boveja | |
| 2005/0131495 A1 | 6/2005 | Parramon et al. | |
| 2006/0217785 A1 | 9/2006 | Matei | |
| 2009/0024179 A1 | 1/2009 | Dronov | |
| 2010/0268309 A1 | 10/2010 | Parramon et al. | |
| 2011/0112610 A1 | 5/2011 | Rahman et al. | |
| 2011/0112612 A1 | 5/2011 | Rahman | |
| 2012/0172948 A1 | 7/2012 | Aghassian | |

FOREIGN PATENT DOCUMENTS

WO     2011097289     8/2011

OTHER PUBLICATIONS

U.S. Appl. No. 61/552,362, filed Oct. 27, 2011, Dronov et al.
International Search Report regarding application No. PCT/US2012/057585 dated Dec. 19, 2012.

* cited by examiner

*Primary Examiner* — George Manuel
(74) *Attorney, Agent, or Firm* — Wong, Cabello, Lutsch, Rutherford & Brucculeri, LLP (57) ABSTRACT

Communication and charging circuitry for an implantable medical device is described having a single coil for receiving charging energy and for data telemetry. The circuitry removes from the AC side of the circuit a tuning capacitor and switch traditionally used to tune the tank circuitry to different frequencies for telemetry and charging. As such, the tank circuitry is simplified and contains no switchable components. A switch is serially connected to the storage capacitor on the DC side of the circuit. During telemetry, the switch is opened, thus disconnecting the storage capacitor from the tank circuit, and alleviating concerns that this capacitor will couple to the tank circuit and interfere with telemetry operations. During charging, the switch is closed, which allows the storage capacitor to couple to the tank circuitry through the rectifier during some portions of the tank circuitry's resonance.

24 Claims, 8 Drawing Sheets

| MODE | M1 | M2 | M3 | M4 |
|---|---|---|---|---|
| ENERGY RECEIVE | OFF | OFF | ON | OFF OR MODULATED (LSK) |
| DATA RECEIVE | OFF | ON | OFF | OFF |
| DATA XMIT | ON | MODULATED | OFF | OFF |

| MODE | M1 | M2 | M5 | M4 |
|---|---|---|---|---|
| ENERGY RECEIVE | OFF | OFF | ON | OFF OR MODULATED (LSK) |
| DATA RECEIVE | OFF | ON | OFF | OFF |
| DATA XMIT | ON | MODULATED | OFF | OFF |

COMMUNICATION AND CHARGING CIRCUITRY FOR A SINGLE-COIL IMPLANTABLE MEDICAL DEVICE

CROSS-REFERENCE TO RELATED APPLICATIONS

The is a non-provisional filing based on U.S. Provisional Patent Application Ser. No. 61/550,588, filed Oct. 24, 2011, which is incorporated by reference and to which priority is claimed.

The present application is related to U.S. Patent Publ. No. 2010/0069992 (the '992 Publication).

FIELD OF THE INVENTION

The present application relates to communication and charging circuitry for a single-coil implantable medical device.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder subluxation, etc. The present invention may find applicability in all such applications and in other implantable medical device systems, although the description that follows will generally focus on the use of the invention in a Bion® microstimulator device system of the type disclosed in U.S. Patent Publ. No. 2010/0268309. The invention can also be used in a Spinal Cord Stimulator (SCS), such as is disclosed in U.S. Pat. No. 7,444,181, for example.

Microstimulator devices typically comprise a small, generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator may have two or more electrodes. Microstimulators benefit from simplicity. Because of their small size, the microstimulator can be directly implanted at a site requiring patient therapy.

Figure 1:
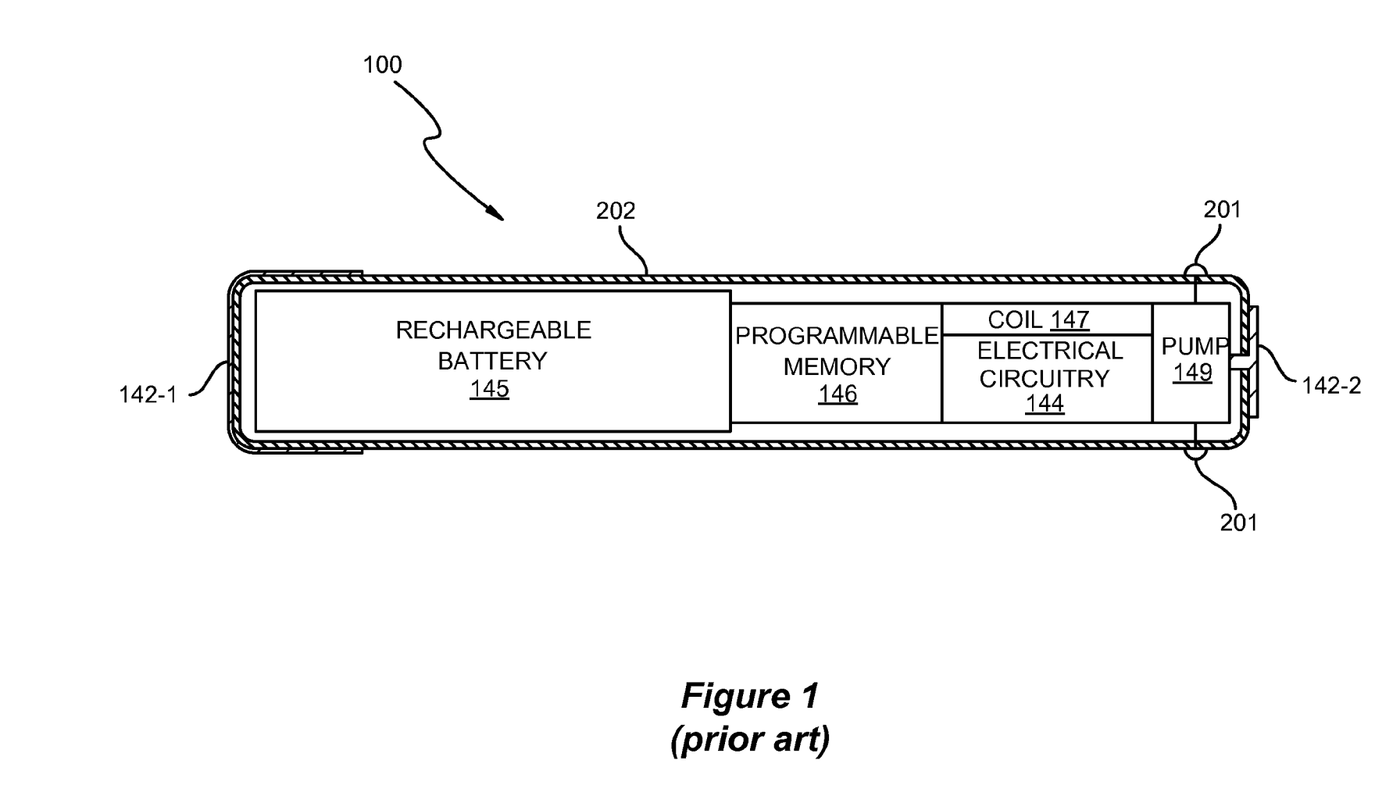
FIG. 1 shows a microstimulator of the prior art.

FIG. 1 illustrates an exemplary implantable microstimulator 100. As shown, the microstimulator 100 includes a power source 145 such as a battery, a programmable memory 146, electrical circuitry 144, and a coil 147. These components are housed within a capsule 202, which is usually a thin, elongated cylinder, but may also be any other shape as determined by the structure of the desired target tissue, the method of implantation, the size and location of the power source 145, and/or the number and arrangement of external electrodes 142. In some embodiments, the volume of the capsule 202 is substantially equal to or less than three cubic centimeters.

The battery 145 supplies power to the various components within the microstimulator 100, such the electrical circuitry 144 and the coil 147. The battery 145 also provides power for therapeutic stimulation current sourced or sunk from the electrodes 142. The power source 145 may be a primary battery, a rechargeable battery, a capacitor, or any other suitable power source. Systems and methods for charging a rechargeable battery 145 will be described further below.

The coil 147 is configured to receive and/or emit a magnetic field that is used to communicate with, or receive power from, one or more external devices that support the implanted microstimulator 100, examples of which will be described below. Such communication and/or power transfer may be transcutaneous as is well known.

The programmable memory 146 is used at least in part for storing one or more sets of data, including electrical stimulation parameters that are safe and efficacious for a particular medical condition and/or for a particular patient. Electrical stimulation parameters control various parameters of the stimulation current applied to a target tissue including the frequency, pulse width, amplitude, burst pattern (e.g., burst on time and burst off time), duty cycle or burst repeat interval, ramp on time and ramp off time of the stimulation current, etc.

The illustrated microstimulator 100 includes electrodes 142-1 and 142-2 on the exterior of the capsule 202. The electrodes 142 may be disposed at either end of the capsule 202 as illustrated, or placed along the length of the capsule. There may also be more than two electrodes arranged in an array along the length of the capsule. One of the electrodes 142 may be designated as a stimulating electrode, with the other acting as an indifferent electrode (reference node) used to complete a stimulation circuit, producing monopolar stimulation. Or, one electrode may act as a cathode while the other acts as an anode, producing bipolar stimulation. Electrodes 142 may alternatively be located at the ends of short, flexible leads. The use of such leads permits, among other things, electrical stimulation to be directed to targeted tissue(s) a short distance from the surgical fixation of the bulk of the device 100.

The electrical circuitry 144 produces the electrical stimulation pulses that are delivered to the target nerve via the electrodes 142. The electrical circuitry 144 may include one or more microprocessors or microcontrollers configured to decode stimulation parameters from memory 146 and generate the corresponding stimulation pulses. The electrical circuitry 144 will generally also include other circuitry such as the current source circuitry, the transmission and receiver circuitry coupled to coil 147, electrode output capacitors, etc.

The external surfaces of the microstimulator 100 are preferably composed of biocompatible materials. For example, the capsule 202 may be made of glass, ceramic, metal, or any other material that provides a hermetic package that excludes water but permits passage of the magnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Figure 2:
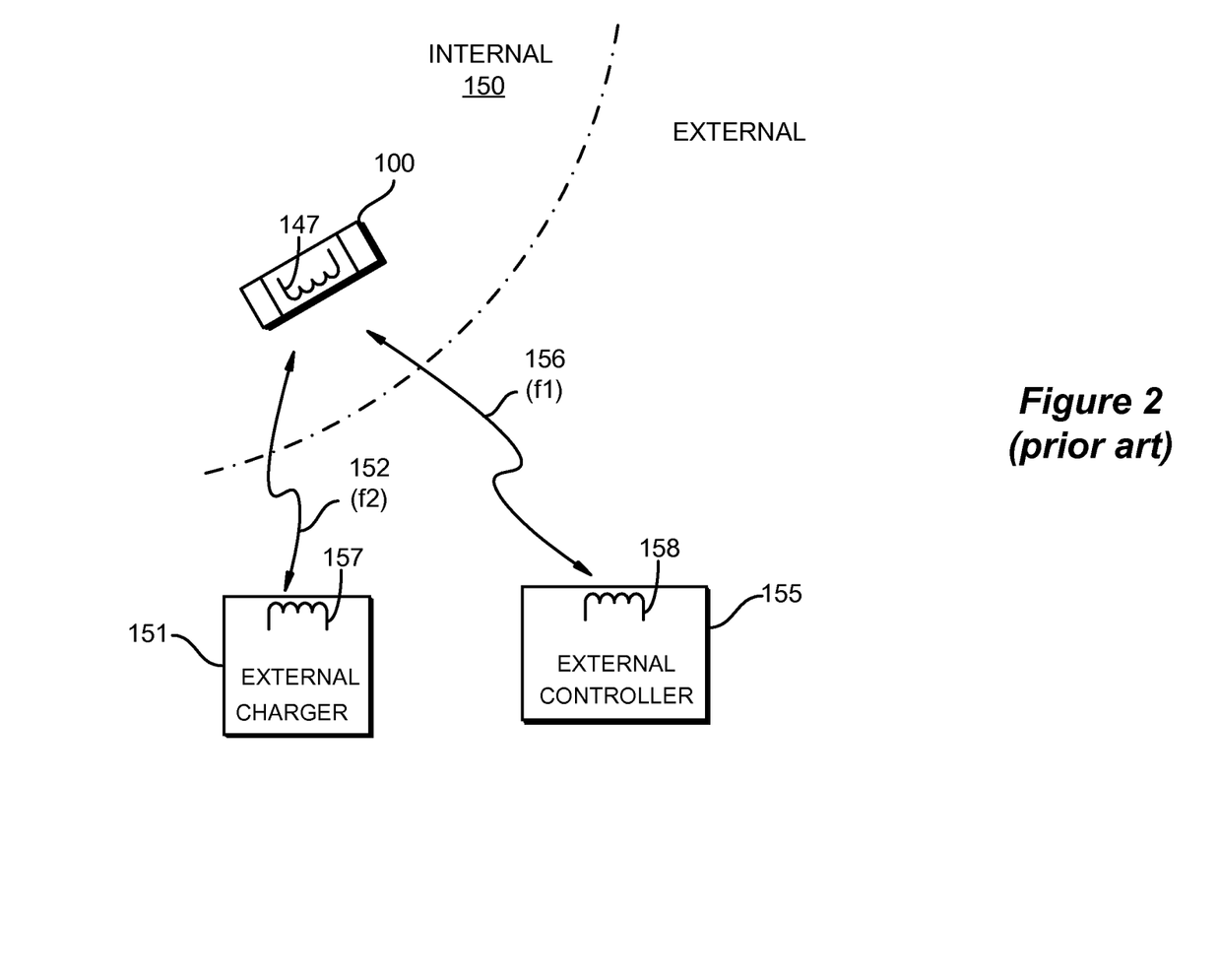
FIG. 2 shows a microstimulator of the prior art as implanted in a patient, as well as an external controller and an external charger.

Turning to FIG. 2, the microstimulator 100 is illustrated as implanted in a patient 150, and further shown are various external components that may be used to support the implanted microstimulator 100. An external controller 155 may be used to program and test the microstimulator 100 via communication link 156. Such link 156 is generally a two-way link, such that the microstimulator 100 can report its status or various other parameters to the external controller 155. Communication on link 156 occurs via magnetic inductive coupling. Thus, when data is to be sent from the external controller 155 to the microstimulator 100, a coil 158 in the external controller 155 is excited to produce a magnetic field that comprises the link 156, which magnetic field is detected at the coil 147 in the microstimulator. Likewise, when data is to be sent from the microstimulator 100 to the external controller 155, the coil 147 is excited to produce a magnetic field that comprises the link 156, which magnetic field is detected at the coil 158 in the external controller. Typically, the magnetic field is modulated, for example with Frequency Shift Keying (FSK) modulation or the like, to encode the data. For example, data telemetry via FSK can occur around a center frequency of f1=125 kHz, with a 129 kHz signal representing transmission of a logic '1' and 121 kHz representing a logic '0'. (This frequency f1 will be discussed as a single frequency defined by its center, but this is merely for convenience; in reality, this frequency has a bandwidth as necessary for FSK communication, and should be so interpreted).

An external charger 151 provides power used to recharge the battery 145 (FIG. 1). Such power transfer occurs by energizing the coil 157 in the external charger 151, which produces a magnetic field comprising link 152, which occurs with a different frequency (f2=80 kHz) than data communications on link 156. This magnetic field 152 energizes the coil 147 through the patient 150's tissue, and which is rectified, filtered, and used to recharge the battery 145. Link 152, like link 156, can be bidirectional to allow the microstimulator 100 to report status information back to the external charger 151. For example, once the circuitry 144 in the microstimulator 100 detects that the power source 145 is fully charged, the coil 147 can signal that fact back to the external charger 151 so that charging can cease. Charging can occur at convenient intervals for the patient 150, such as every night.

Figure 3A:
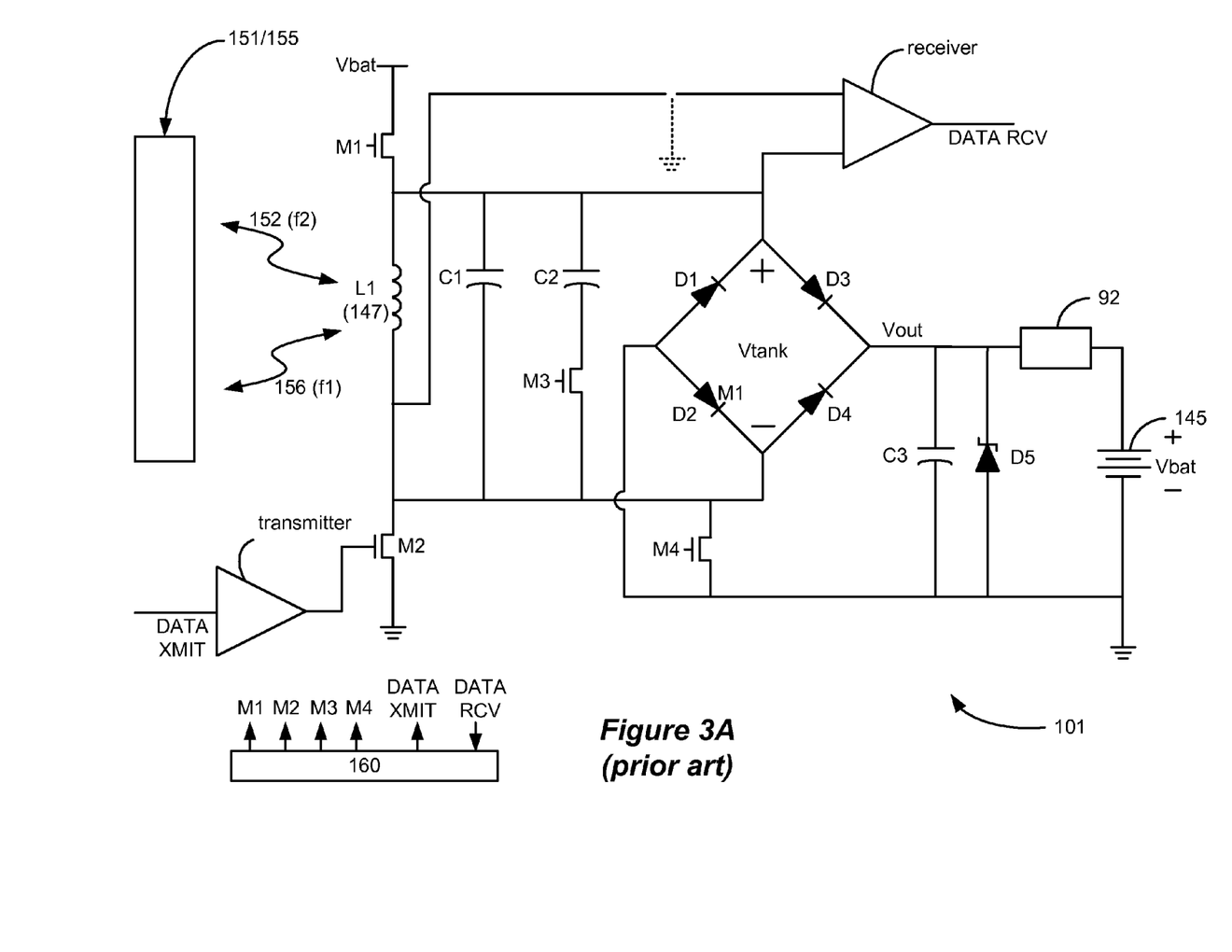
FIGS. 3A and 3B shows the communication and charging circuitry in the microstimulator of the prior art, and the various modes in which such circuitry can be operated.

FIG. 3A shows the communication and charging circuitry 101 within microstimulator 100 that is coupled to coil 147. Such circuitry is explained in detail in the '992 Publication, with which the reader is assumed familiar, and thus is only briefly explained here.

As explained in the '992 Publication, the circuitry of FIG. 3A is beneficial because it uses a single coil L1 (147) for receiving a magnetic charging field 152 from the external charger 151, and for transmitting and receiving data telemetry 156 to and from the external controller 155. (The external charger 151 and external controller 155 are shown in FIG. 3A as one integrated unit for simplicity).

Coil 147 is connected at one end through transistor switch M1 to a voltage, Vbat, provided by the battery 145 in the microstimulator 100. Coil 147 is connected at its other end through transistor switch M2 to ground. Tank capacitor C1 is connected in parallel with coil 147, and tunes the coil to a particular frequency for transmitting or receiving data telemetry to and from the external controller 155 (e.g., approximately f1=125 kHz). A series combination of a tuning capacitor C2 and transistor switch M3 are also connected in parallel to coil 147. Transistor M3 is turned on during receipt of a magnetic charging field along link 152 from the external charger 151 to tune the coil to the frequency of the magnetic charging filed (e.g., approximately f2=80 kHz). Also connected in parallel with coil 147 is a full bridge rectifier formed of diodes D1-D4 for producing DC voltage Vout. A half bridge rectifier or even a signle diode rectifier could also be used. A transistor switch M4 is also connected between the rectifier circuitry and ground.

DC voltage Vout is received at storage capacitor C3, which filters and smoothes the voltage before being passed to battery charging circuitry 92. Battery charging circuitry 92 is used to charge the battery 145 in a controlled fashion. If needed, a Zener diode D5 or other suitable voltage clamp circuit may be connected across storage capacitor C3 to prevent Vout from exceeding some predetermined value.

Figure 3B:
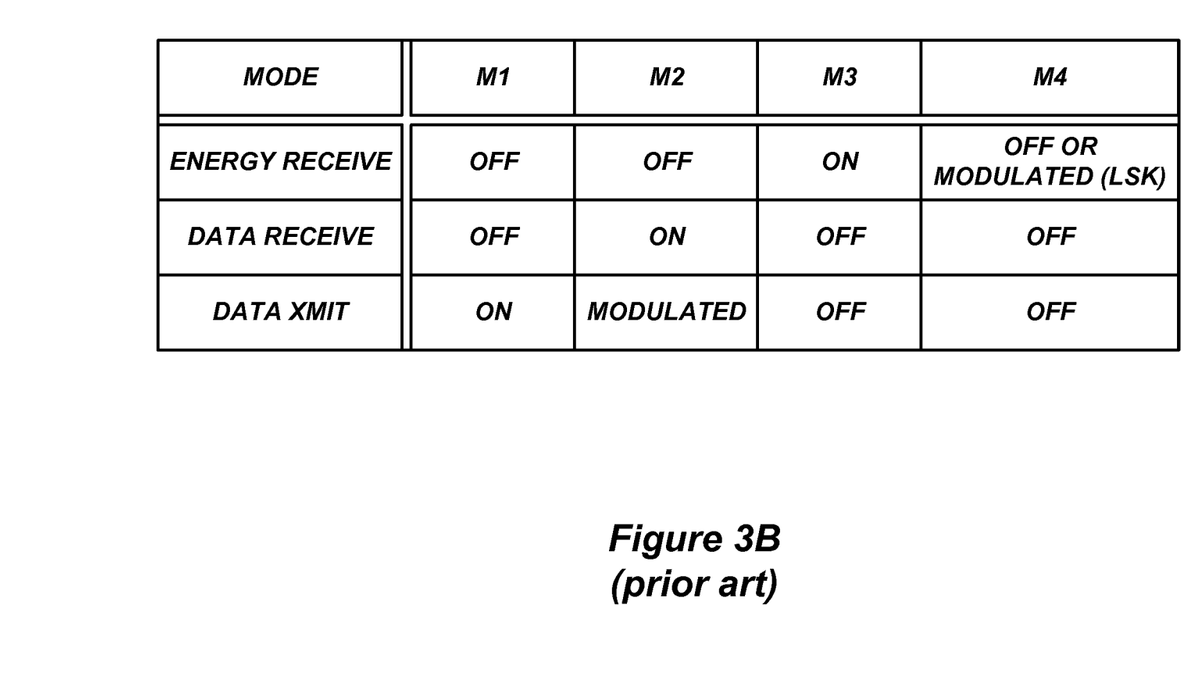

FIG. 3B shows the status of transistor switches M1-M4 for the energy receive, data receive, and data transmit modes. As shown, to operate in an energy receive mode, the circuit will turn switches M1, M2 and M4 OFF, and will turn switch M3 ON. Turning M3 ON includes tuning capacitor C2 in parallel with tank capacitor C1, which, in conjunction with the inductance formed by the coil 147, forms a resonant circuit which is tuned to the frequency of the magnetic charging field (f2=80 kHz). The circuit of FIG. 3A may also operate in a data transmit mode during charging by employing back telemetry known as Load Shift Keying (LSK), in which case transistor M4 is modulated with the data to be transmitted back to the external charger 151.

For the circuit of FIG. 3A to operate in a data receive mode, the circuit will turn switches M1, M3 and M4 OFF, and will turn switch M2 ON. Turning M3 off excludes capacitor tuning C2 from the resonant circuit, whose tuning is thus governed by coil 147 and tank capacitor C1. With tuning capacitor C2 excluded, the resonant circuit is tuned to a higher frequency matching the operation of the external controller 155 (f1=125 kHz). Turning M2 ON grounds the resonant circuit, which provides an input to the receiver, which demodulates the received data (DATA RCV). The receiver can either comprise a differential input as illustrated in solid lines in FIG. 3A, or can comprise a single-ended non-differential input in which one of the inputs is grounded, as shown in dotted lines in FIG. 3A.

As further shown in FIG. 3B, the circuit of FIG. 3A may also operate in a data transmit mode by turning switches M3 and M4 OFF, by modulating switch M2 with a data signal (DATA XMIT), and by turning switch M1 ON. Under these conditions, the resonant circuit is once again, by virtue of transistor M3 being OFF, tuned to the higher frequency (f1=125 kHz), and will broadcast a signal to the external controller 155 along link 156 accordingly, with the energy for the radiation being supplied from the battery voltage, Vbat, via transistor M1. The transmitter receiving the data to be transmitted (DATA XMIT), is shown coupled to transistor M2, but could also couple to transistor M1.

Thus, it is seen that by selectively controlling the state of the switches M1-M4, the circuit of FIG. 3A may operate in different modes, using only a single coil 147. Such modes may be invoked in a time-multiplexed manner, e.g., with a first mode being followed by a second mode, depending upon the particular application at hand. Control signals M1-M4, as well as DATA XMIT, are ultimately issued by a microcontroller (or, more generically, control circuitry 160) in the microstimulator 100, and DATA RCV is received by that microcontroller.

While the versatility of the single-coil, multi-function circuit of FIG. 3A is desirable, the inventors recognize drawbacks. One drawback is that storage capacitor C3 loads the resonant tank circuit (coil L1 147 and tank capacitor C1) during periods when the circuitry transmits data. As discussed earlier, during data transmission, switch M1 is closed while switch M2 is modulated with the data signal, which causes the tank circuit to resonate, thus forming an AC voltage, Vtank, with a center frequency of approximately f1=125 kHz. This alternating voltage in the tank circuit also appears across the full bridge rectifier (D1-D4). Because switch M1 is closed, the top node of the tank circuit, which node is connected to the switch M1, will remain fixed to approximately Vbat. As a result, there will be some charge leakage from this node to the storage capacitor C3 via diode D3. Because switch M2 is modulated, the voltage at the bottom node of the tank circuit, which node is connected to the switch M2, will vary between ground and Vbat. Thus, depending upon the instantaneous voltages at the bottom node and Vout, diode D4 may also become forward biased and leak charge into the storage capacitor C3. Note that diodes D1 and D2 do not conduct because they remain reversed biased. Thus, some of the charge generated in the resonant tank circuit is leaked into the storage capacitor C3, which loads the resonant tank circuit. (Other components on the DC side of the rectifier such as the battery charging circuitry 92 and the battery 145 may be disconnected or disabled during telemetry, and in any event do not appreciably load the tank circuit).

The inventors have noticed that loading of the tank circuit by the storage capacitor C3 has undesirable effects. The first relates to the speed at which the RF signal transmitted by the tank circuit—i.e., the RF signal comprising communication link 156—can reach its full strength. The strength of the RF signal is primarily governed by the magnitude of Vtank. But leakage to the storage capacitor C3 via the full bridge rectifier impedes a full strength RF signal, at least initially. This is because storage capacitor C3 is initially not charged, and such lack of charge promotes leakage through the diodes D3 and D4 as previously discussed. Eventually such leakage will charge the storage capacitor C3, which will tend to reduce the leakage through the diodes, at which point the RF signal will be at full strength. The effect is that when circuit of FIG. 3A begins to transmit data, an initial portion of the data will not be transmitted with a full strength RF signal. This makes reception of this signal at the external controller 155 more difficult to resolve, resulting in corrupted data or no data at all. Experimental results show that the length of time for the tank circuit to transmit with a full strength RF signal is approximately 2 ms. At typical data transmission rates of 4 Kbps, this delay can contribute to significant data transmission errors affecting 8 bits of information in this example. Moreover, even if storage capacitor C3 is fully charged, there can still be some leakage through the diodes in the rectifier, and hence some coupling of the storage capacitor C3 to the tank circuit, which impeded RF signal strength and detunes the tank circuit.

A second undesirable effect is that loading of the tank circuit alters its resonant frequency, especially during the time when the RF signal strength is increasing towards its maximum value. This occurs because leakage through the didoes D3 and D4 effectively places storage capacitor C3 in parallel with the tank circuit. This increases the effective capacitance of the tank circuit, which decreases its resonant frequency. In short, coupling of the storage capacitor C3 detunes the tank circuitry to less than the optimal center value of f1=125 KHz. Again, such detuning can affect the reliability of data transmission.

Another drawback of the circuit of FIG. 3A relates to switch M3 on the AC side of the rectifier. Vtank can comprise a relatively high alternating voltage, and switch M3 is therefore subject to large swings in voltage. This makes implementing and controlling switch M3 rather difficult, and can result in increased complexity, size, and cost of the circuitry.

This disclosure presents solutions to the aforementioned and other shortcomings of the prior art.

DETAILED DESCRIPTION OF THE INVENTION

Improved communication and charging circuitry for an implantable medical device is described having a single coil for receiving charging energy and for data telemetry. The circuitry removes from the AC side of the circuit a tuning capacitor and switch traditionally used to tune the tank circuitry to different frequencies for telemetry and charging. As such, the tank circuitry is simplified and contains no switchable components that can be difficult to implement. A switch is serially connected to the storage capacitor on the DC side of the circuit, which essentially takes the place of the switch of the prior art by tuning the circuit for telemetry or charging. During telemetry, the switch is opened, thus disconnecting the storage capacitor from the tank circuit, and alleviating concerns that this capacitor will couple to the tank circuit and interfere with telemetry operations. During charging, the switch is closed, which allows the storage capacitor to couple to the tank circuitry through the rectifier during some portions of the tank circuitry's resonance. As such, previously undesired coupling through the rectifier in the prior art is put to the useful purpose of tuning the tank circuitry to an appropriate frequency during charging. Because the switch is moved to the DC side of the circuit, it is not subject to high voltage swings, and thus is simpler and less costly to implement.

Figure 4A:
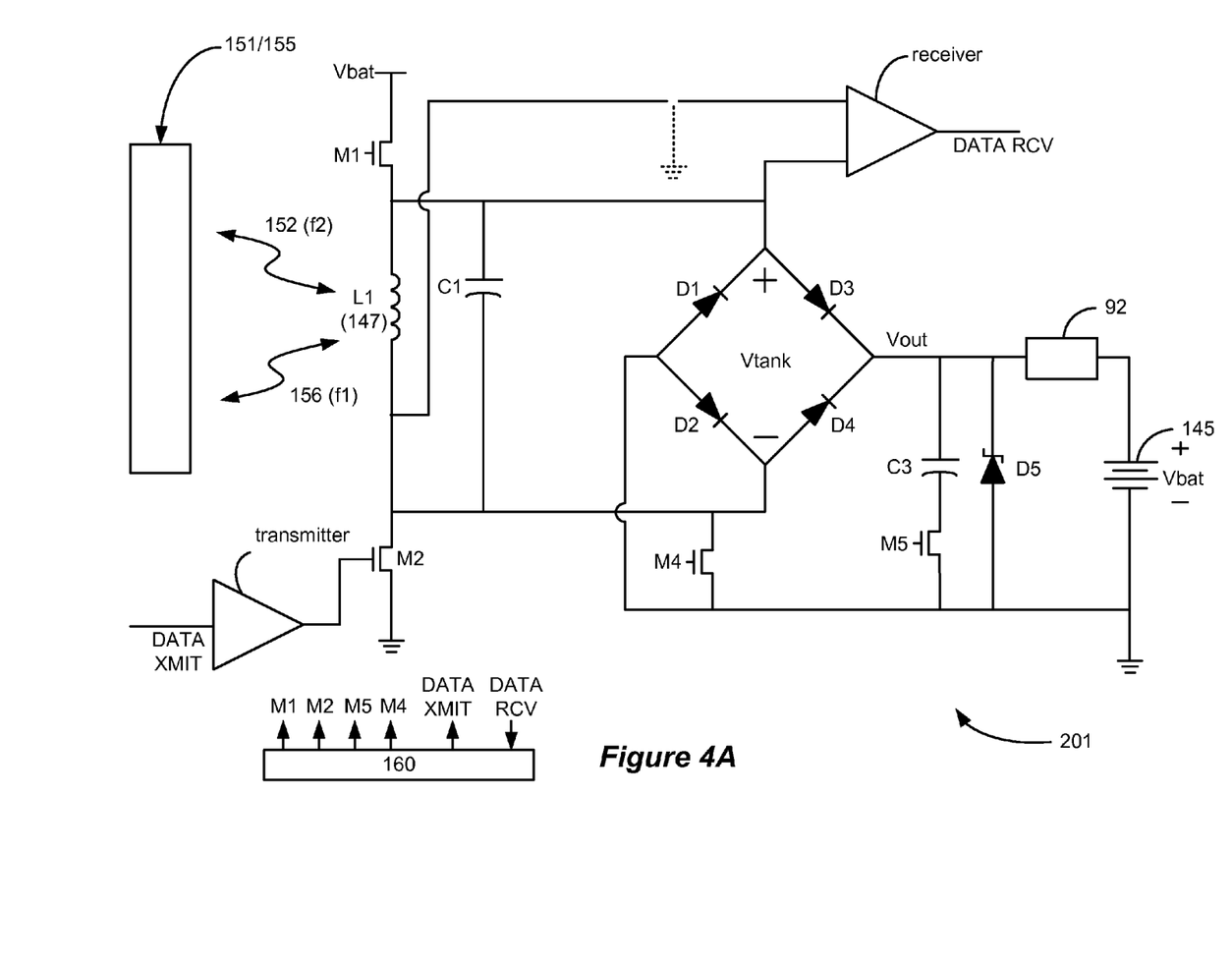
FIGS. 4A and 4B shows improved communication and charging circuitry, and the various modes in which such circuitry can be operated.

One embodiment of improved communication and charging circuitry 201 is shown in FIG. 4A. Many of the components in circuit 201 are similar to the corresponding components in circuit 101 of FIG. 3A. However, there are differences. First, circuit 201 does not include a tuning capacitor C2 and its associated switch M3. As a result, the resonant tank circuit includes only coil L1 and tank capacitor C1, and no other circuitry is connected to the tank circuitry to tune its resonance. Second, a switch M5 is placed in series with the storage capacitor C3. Thus, storage capacitor C3 is connected to the rest of the circuit when switch M5 is on, and is disconnected when M5 is off. The relevance and functionality of including or discluding storage capacitor C3 in the circuit will be discussed subsequently.

Figure 4B:
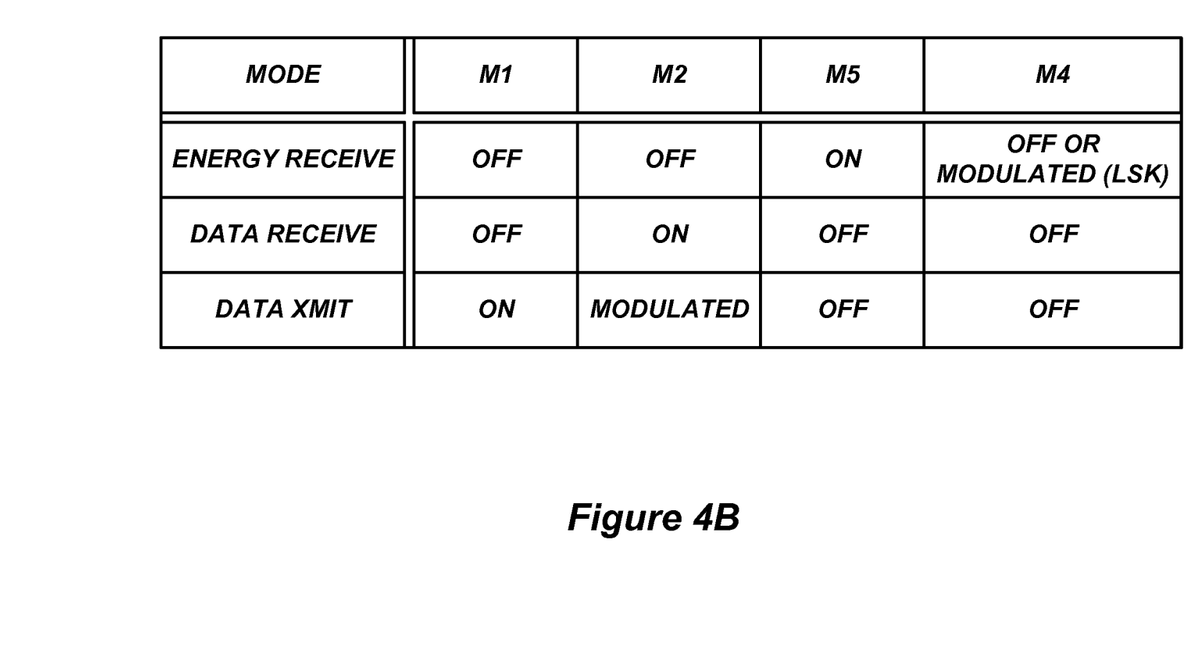

FIG. 4B shows the status of transistor switches M1, M2, M4, and M5 for the energy receive, data receive, and data transmit modes. The status of switches M1, M2, and M4 in circuit 201 do not change from circuit 101 (compare FIG. 3B), and as such these switches are still similarly controlled to implement the energy receive, data receive, and data transmit operations. New switch M5 in circuit 201 is also similarly controlled to switch M3 in circuit 101, in that it is off during data telemetry, and on during charging. However, as will be seen, repositioning of this switch to the DC side of the rectifier has operational and manufacturing advantages. As in circuit 101, 201 uses control circuitry 160 to issue the various control signals M1, M2, M4, and M5 and to handle telemetered data.

During telemetry operations, the tank circuit formed by coil L1 and tank capacitor C1 has values selected as suitable for resonating at a frequency suitable for FSK telemetry (e.g., f1=125 kHz). As mentioned, during data telemetry, switch M5 is turned off, thus disconnecting the storage capacitor C3 from the AC side of the circuit 201. Thus, unlike the circuit 101 of FIG. 3A, the storage capacitor C3 does not load the tank circuit during telemetry operations. As such, problems discussed above with respect to the prior art circuit 101 are alleviated: circuit 201 can quickly build up power in the tank circuit, such that the resulting RF signal can ramp up to full strength much more quickly. For example, experimental results show that the length of time for the tank circuit to transmit with a full strength RF signal is approximately only 200 microseconds, a ten-fold improvement over the 2 milliseconds required for the circuit 101 of FIG. 3A. Moreover, because the storage capacitor is decoupled, it does not increase the capacitance of the tank circuitry, and thus will not detune its frequency. This improves the reliability and stability of data telemetry, particularly during modes in which the microstimulator 100 must transmit data to the external controller 155.

During the receipt of a charging field from the external controller 151, i.e., during the energy receive mode, M5 is closed as mentioned, which couples storage capacitor C3 into the circuit. As before, storage capacitor C3 filters and smoothes the DC voltage (Vout) provided by the rectifier, which voltage can then be used to charge the battery 145 in the microstimulator 100. Additionally, storage capacitor C3 is used to tune the resonance during energy receipt. For example, the circuit 201 is tuned to resonate at approximately f2=80 kHz during this mode, to match the frequency of the magnetic charging field provided by the external charger 151 along link 152.

Figure 5:
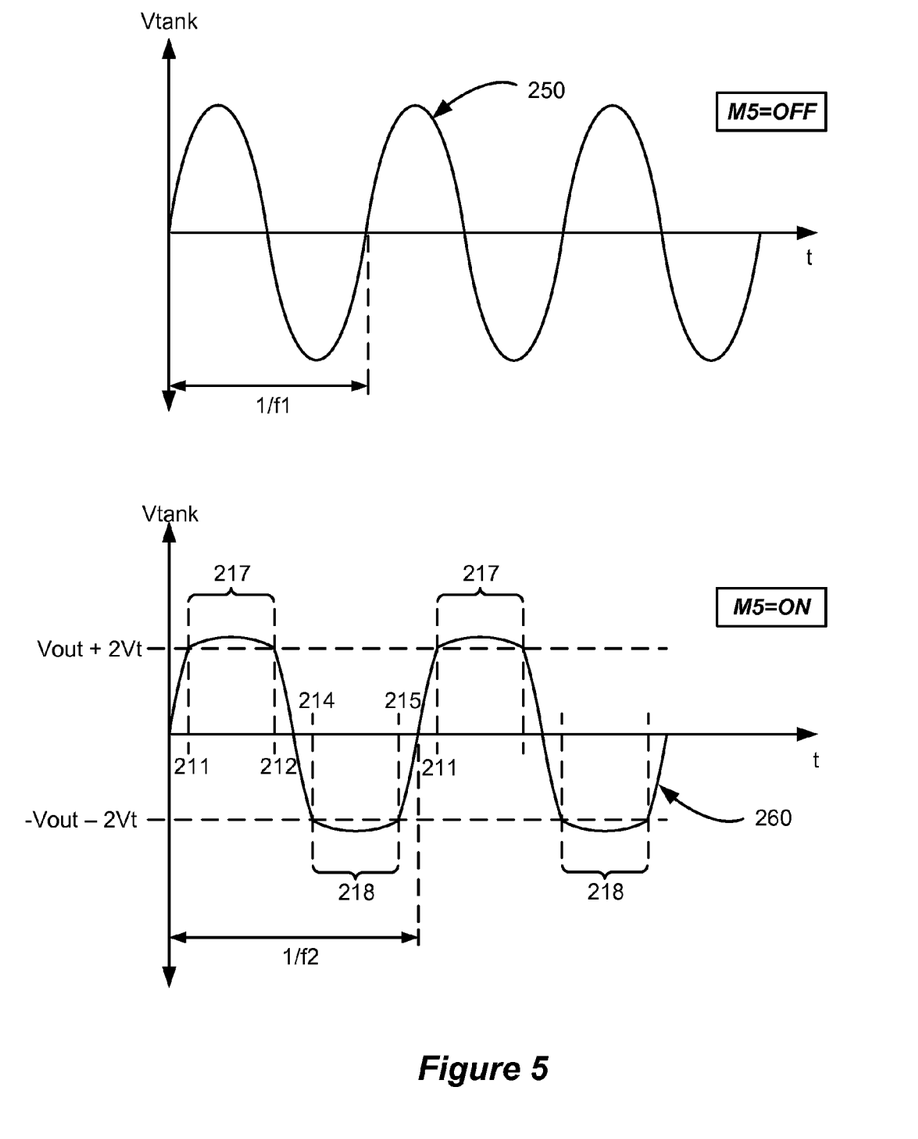
FIG. 5 shows differences in the voltage of the tank circuitry during data telemetry and energy receive modes using the improved circuitry of FIG. 4A.

How this tuning occurs—i.e., how the storage capacitor C3 is used to load the tank in the energy receive mode—is explained with reference to FIG. 5. Waveform 250 shows Vtank during data telemetry modes, i.e., during data receive or data transmit, when switch M5 is off. In this instance, storage capacitor C3 is not loaded, and the tank circuit resonates at a frequency f1 in accordance with the inductance of the coil 147 and the tank capacitor C1. As one skilled will appreciate, there may be other parasitic capacitances arising from the didoes D1-D4 in the rectifier, from the battery charging circuitry 92, or from the battery 145 in the microstimulator 100, which other parasitic capacitances could affect the tuning of the resonance of the tank circuit should coupling to the tank circuit occur through the rectifier. However, such parasitic capacitances can be modeled or determined experimentally to assess their overall effect on the capacitance of the circuit 201. If significant, the value of tank capacitor C1 can be adjusted as necessary to compensate for any parasitic capacitance, and to tune the circuit 201 to its desired frequency, e.g., to f1=125 kHz. As stated earlier, using switch M5 to prohibit coupling of the storage capacitor C3 during data telemetry modes alleviates the telemetry problems of the prior art discussed earlier.

Waveform 260 shows Vtank during the energy receive mode, when switch M5 is on. After some cycles of Vtank, it can be assumed that the storage capacitor C3 has been charged to a value of Vout, perhaps 5V or so. As Vtank increases during its positive cycle, the voltage across the rectifier is not sufficient to cause leakage through the diodes, and thus Vtank increases similarly to waveform 250. At time 211 however, the voltage is sufficient to cause leakage through diodes D3 and D2, at which point the storage capacitor C3 loads the tank circuit. Assuming the diodes have a forward voltage drop of Vt, this critical voltage equals Vout+2Vt. Thus, during period 217 when this critical voltage is exceeded, storage capacitor C3 is effectively paralleled with the tank circuit. As a result, and as shown in FIG. 5, the instantaneous resonant frequency of the tank circuit decreases, perhaps by as much as a factor of 10. This flattens and stretches the shape of the waveform 260 during period 217, and increases its duration compared to waveform 250.

As Vtank decreases, it reaches time 212, at which point the critical voltage is no longer exceeded. Thus from time 212 to 214, the storage capacitor C3 is once again decoupled, and the circuit 201 once again behaves similarly to waveform 250. Eventually, during its negative cycle, Vtank reaches the negative of the critical voltage (−Vout−2Vt), which forward biases diodes D4 and D1. Once again, the storage capacitor C3 is coupled to the tank circuit during period 218, which again decreases the resonant frequency and flattens and stretches the waveform. When Vtank eventually increases, this critical negative voltage is no longer exceeded, and from time 215 to 211 the waveform 260 again mimics waveform 250, etc.

The overall effect provided by purposefully allowing coupling of the storage capacitor C3 to the tank circuit for the higher voltage portions of the Vtank cycle is that the overall frequency of the waveform 260 is decreased to a frequency matching that of the incoming magnetic charging field, i.e., f2=80 kHz. As with the tank capacitor C1, modeling or experimentation can be used to choose the value of storage capacitor C3 to achieve this desired charging frequency. In one example, and assuming a coil L1 inductance of 80 µH, tank capacitor C1 can comprise 33 nF, and storage capacitor C3 can comprise 4.7 µF. Experimental data has shown that the reduction in resonant frequency due to the loading effect of the storage capacitor C3 and related parasitics is approximately 20%, which is suitable for the implantable medical device telemetry/charging applications at hand.

Thus, improved communication and charging circuit 201 supports separately-tunable data telemetry and charging functions, and does so without loading the tank circuitry during telemetry. Moreover, providing switch M5 on the DC side of the circuit means that that switch is subject to much smaller DC voltages, is more easily controllable using standard logic levels at its gate, and can be made smaller when compared with switch M3 of the prior art. Thus, microstimulator complexity, size, and cost are beneficially lowered.

Figure 6:
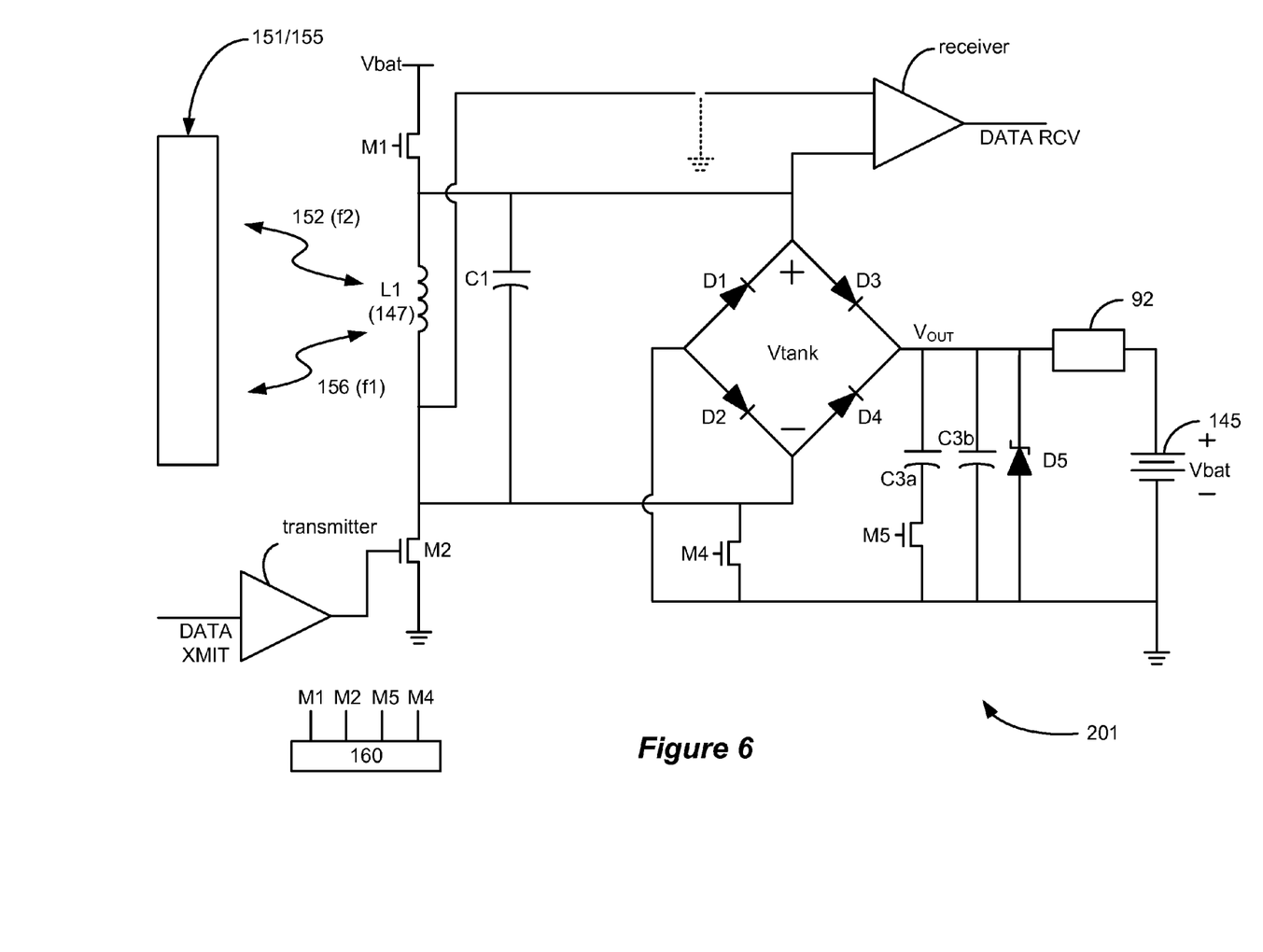
FIG. 6 shows an alternative to the improved circuitry of FIG. 4A.

One skilled in the art will recognize that circuit 201 can be modified in various ways. For example, because data transmission from the microstimulator is a particular problem, it may only be necessary to open switch M5 during transmission, i.e., it may be acceptable that switch M5 is closed during periods of data reception, when Vtank may be at lower voltages and thus coupling to the storage capacitor is not as big a concern. The circuitry to transmit and receive data can interface with the tank circuitry in different ways, and it is not necessary place switches M1 and M2 in the exact configuration shown; other configurations for the receiver and transmitter circuitry can be used. Battery charging circuitry 92 is not strictly necessary and need not necessarily be placed in line with the battery 145. The tank circuit need not necessarily comprise a paralleled configuration of coil L1 and tank capacitor C1, and instead series configurations can be used. If helpful in tuning the telemetry and energy frequencies f1 and f2, both a switched storage capacitor C3a and a non-switch storage capacitor C3b can be used on the DC side of the rectifier, as shown in FIG. 6. This configuration may still allow storage capacitor C3b to be coupled to the tank circuit during telemetry if useful for tuning, but the value of this capacitor could be reduced; storage capacitor C3a could still be controlled by switch M5 depending on whether telemetry or energy reception is occurring, as previously discussed. Or, the switch M3 and tuning capacitor C2 from circuit 101 can still be included along with the switch M5 and storage capacitor C3 from circuit 201, with both switches being selectively controlled during telemetry or energy receive modes. Still other configurations of the capacitors on both the AC and DC sides of the rectifier are possible.

While the invention herein disclosed has been described by means of specific embodiments and applications thereof, numerous modifications and variations could be made thereto by those skilled in the art without departing from the scope of the invention set forth in the claims.

What is claimed is:

1. Communication and charging circuitry for an implantable medical device, comprising:
   a resonant circuit comprising a coil and a resonant capacitor for producing an AC voltage;
   a rectifier coupled to the resonant circuit for producing a DC voltage from the AC voltage;
   a storage capacitor for receiving the DC voltage;
   a first switch in series with the storage capacitor; and
   control circuitry, wherein the control circuitry is configured to close the first switch during periods when the resonant circuit is wirelessly receiving energy, and wherein the control circuitry is configured to open the first switch during periods where the resonant circuit is performing data telemetry.

2. The circuitry of claim 1, wherein the coil and the resonant capacitor are coupled in parallel.

3. The circuitry of claim 1, further comprising a battery, wherein the DC voltage is used to charge the battery.

4. The circuitry of claim 3, further comprising battery charging circuitry, wherein the battery charging circuitry is in line between the DC voltage and the battery.

5. The circuitry of claim 1, further comprising a transmitter, wherein the transmitter is coupled to the resonant circuit to cause the resonant circuit to resonate and wirelessly transmit data.

6. The circuitry of claim 1, further comprising a receiver, wherein the receiver is coupled to the resonant circuit to receive resonance in the resonant circuit when the resonant circuit is wirelessly receiving data.

7. The circuitry of claim 1, further comprising a second switch coupled between a voltage of the battery and a first end of the resonant circuit, and a third switch coupled between ground and a second end of the resonant circuit, wherein a transmitter is configured to control either the second switch or the third switch.

8. The circuitry of claim 7, wherein the control circuitry is configured to open the second and third switches during periods when the resonant circuit is wireless receiving energy.

9. The circuitry of claim 7, wherein data telemetry comprises a data transmit mode and a data receive mode, and wherein during the data transmit mode the control circuitry is configured to modulate with data the second or third switch coupled to the transmitter and to close the other of the second or third switch, and wherein during the data receive mode the control circuitry is configured to close either of the second or third switches.

10. The circuitry of claim 1, wherein the rectifier comprises a full bridge rectifier.

11. The circuit of claim 1, wherein no circuitry is connected to the resonant circuit to tune a resonant frequency of the resonant circuit.

12. Communication and charging circuitry for an implantable medical device, comprising:
    a resonant circuit comprising a coil and a resonant capacitor for producing an AC voltage;
    a rectifier coupled to the resonant circuit for producing a DC voltage from the AC voltage; and
    tuning circuitry comprising a storage capacitor and coupled to the output of the rectifier, wherein the tuning circuitry is controllable to control a resonant frequency of the resonant circuit.

13. The circuitry of claim 12, wherein the tuning circuitry is configured to control the resonant frequency of the resonant circuit to a first frequency in a first mode of operation, and to a second frequency in a second mode of operation.

14. The circuitry of claim 12, wherein the first mode comprises data telemetry, and wherein the second mode comprises an energy receive mode.

15. The circuitry of claim 14, further comprising a battery, wherein during the energy receive mode the DC voltage is used to charge the battery.

16. The circuitry of claim 15, further comprising battery charging circuitry, wherein the battery charging circuitry is in line between the DC voltage and the battery.

17. The circuitry of claim 12, wherein the coil and the resonant capacitor are coupled in parallel.

18. The circuitry of claim 12, further comprising a transmitter, wherein the transmitter is coupled to the resonant circuit to cause the resonant circuit to resonate and wirelessly transmit data.

19. The circuitry of claim 12, further comprising a receiver, wherein the receiver is coupled to the resonant circuit to receive resonance in the resonant circuit when the resonant circuit is wirelessly receiving data.

20. The circuitry of claim 12, further comprising a second switch coupled between a voltage of the battery and a first end of the resonant circuit, and a third switch coupled between ground and a second end of the resonant circuit, wherein a transmitter is configured to control either the second switch or the third switch.

21. The circuitry of claim 20, wherein the second and third switches are opened when the resonant circuit is wireless receiving energy.

22. The circuitry of claim 20, wherein during a data transmit mode the second or third switch coupled to the transmitter is modulated with data and the other of the second or third switch is closed, and wherein during a data receive mode either of the second or third switches is closed.

23. The circuitry of claim 12, wherein the rectifier comprises a full bridge rectifier.

24. The circuit of claim 12, wherein no circuitry is connected to the resonant circuit to tune a resonant frequency of the resonant circuitry.

\* \* \* \* \*